United States Patent [19]

Jessel, Jr. et al.

[11] Plant 4,299

[45] Sep. 12, 1978

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 833,376

[22] Filed: Sep. 14, 1977

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Beall & Jeffery

[57] ABSTRACT

A chrysanthemum cultivar particularly characterized as to uniqueness by the combined characteristics of flat capitulum form; daisy capitulum type; white ray floret color; diameter across face of capitulum ranging from 100 to 120 mm. at maturity; uniform 7 week photoperiodic flowering response to short days; tall plant height when grown as a single stem cut spray; and semi-upright branching pattern.

7 Drawing Figures

The present invention comprises a new and distinct cultivar of *Chrysanthemum morifolium,* Ramat., hereinafter referred to by the cultivar name Superstar (#74028002).

Superstar is a product of a planned breeding program which had the objective of creating new chrysanthemum cultivars with daisy capitulum type, with white ray floret color, with 7 and/or 8 week flowering response, and with the ability to produce commercially acceptable quality in year round cut mum programs. Such traits in combination were not present in previously available commercial cultivars.

Superstar was originated from a cross made in a controlled breeding program in Barberton, Ohio in 1972. The female parent was #71133006 (unnamed seedling), a white daisy originated by the present inventors from a cross between Nimrod (#60092002; unpatented; commercially available) and Sovereign (#5676001; unpatented; commercially available). The male parent of Superstar was Celebration (#70123008; U.S. Plant Pat. No. 3,778), a yellow daisy. Nimrod, Sovereign, and Celebration were all products of the breeding program of the present inventors.

Superstar was discovered and selected as one flowering plant within the progeny of the stated cross by Walter H. Jessel, Jr. and William E. Duffett on Nov. 26, 1974 in a controlled environment in Barberton, Ohio.

The first act of asexual reproduction of Superstar was accomplished when vegetative cuttings were taken from the initial selection in February, 1975 in a controlled environment in Barberton, Ohio, by a technician working under formulations established and supervised by Walter H. Jessel, Jr. and William E. Duffett. Horticultural examination of selected units initiated Mar. 15, 1976 has demonstrated that the combination of characteristics as herein disclosed for Superstar are firmly fixed and are retained through successive generations of asexual reproduction.

Superstar has not been observed under all possible environmental conditions. The phenotype may vary significantly with variations in environment such as temperature, light intensity, and day length. The following observations, measurements, and comparisons describe plants grown in Barberton, Ohio under greenhouse conditions which approximate those generally used in commercial practice, as described in Chart A which appears at the end of the present specification. A light intensity chart of general use is shown in ASHAE Trans., Vol. 64, pg. 64 and reference is made thereto.

The following traits have been repeatedly observed and are determined to be basic characteristics of Superstar which in combination distinguish this chrysanthemum as a new and distinct cultivar:

1. Flat capitulum form.
2. Daisy capitulum form.
3. White ray floret color.
4. Yellow-green (immature) to yellow (mature) disc floret color.
5. Diameter across face of capitulum ranging from 100 to 120 mm. at maturity.
6. Uniform 7 week photoperiodic flowering response to short days.
7. Tall plant height (requiring 1 to 2 long day weeks prior to short days to attain a flowered plant height of 72 to 82 cm. for November through April flowerings).
8. Semi-upright branching pattern.

The accompanying photographic drawings show typical inflorescence and foliage characteristics of Superstar with colors being as nearly true as possible with illustrations of this type. Sheet 1 is a color photograph of Superstar. Sheet 2 is a black and white photograph showing three views of the inflorescence of Superstar. Sheet 3 is a black and white photograph showing the foliage of Superstar at three stages of growth.

Of the many commercial cultivars known to the present inventors, the most similar existing cultivar in comparison to Superstar is the cultivar White Marble (#54318B08; unpatented). Reference is made to attached Chart B which compares certain characteristics of Superstar to those same characteristics of White Marble. General comparisons are as follows:

In comparison to White Marble, Superstar has larger capitulum size and earlier flowering response. The ray floret color, capitulum form, capitulum type, and plant height of Superstar are similar to those of White Marble.

In the following description, color references are made to The Munsell Color Cascade, 1972 edition. The color values were determined between 8:30 and 9:00 A.M. on Apr. 21, 1977 under 150 foot-candle light intensity at Barberton, Ohio.

Botanical Classification: *Chrysanthemum morifolium,* Ramat., cv Superstar.

INFLORESCENCE

A. Capitulum (See Sheets 1 and 2 of drawings):
*Form.*—Flat.
*Type.*—Daisy.
*Diameter across face.*—100 to 120 mm.

B. Corolla of ray florets:
*Persistence.*—Resists shatter.
*Color (abaxial).*—26-2 to white.
*Color (adaxial).*—26-1 to white.

C. Reproductive organs:
*Androecium.*—Present disc florets only; scant to numerous; scant pollen.
*Gynoecium.*—Present both ray and disc florets.

PLANT

General appearance: Semi-upright branching pattern; tall height.

B. Foliage (See Sheets 1 and 3):
*Color abaxial.*—Approximately 21-14 to 22-14.
*Color adaxial.*—Approximately 21-13 overlaid with white.

CHART A

| | Average Greenhouse Chrysanthemum Environments Used For Barberton, Ohio | | | | | |
|---|---|---|---|---|---|---|
| | Temperatures Used | | | | | |
| SEASON | Night | Bright Day | Cloudy Day | Lighting Used | Black Cloth Used | SUPP $CO_2$ |
| FALL | 65° F to 56° F | 65° F to 80° F | 60° F to 75° F | 2 to 4 weeks at 3 Hours Per Night of 7–10 f.c. | To Sept. 15 on-5:30 PM Off-7:30 AM | From Oct. 15 300 ppm |
| WINTER | 58° F to 62° F | 65° F to 70° F | 60° F to 65° F | 2 to 5 weeks at 5 hours Per Night of 7–10 f.c. | NONE | 300 ppm |
| SPRING | 58° F to 65° F | 65° F to 80° F | 60° F to 75° F | 2 to 4 weeks at 5 Hours Per Night of 7–10 f.c. | From Mar. 15 on-5:30 PM Off-7:30 AM | To Apr. 15 300 ppm |
| SUMMER | 62° F to 68° F | 70° F to 90° F | 65° F to 75° F | 1 to 2 weeks at 3 Hours Per Night of 7–10 f.c. | on-6:00 PM Off-8:00 AM | NONE |

CHART B

| COMPARISON OF SUPERSTAR AND WHITE MARBLE | | | | | |
|---|---|---|---|---|---|
| Cultivar | Ray Floret Color | Capitulum Form And Type | Diameter Across Face Of Capitulum | Plant Height | Flowering Response Period |
| Superstar | White | Flat Daisy | 100 to 120 mm. | Tall | 7 week |
| White Marble | White | Flat Daisy | 70 to 85 mm. | Tall | 9 week |

Comparisons Made Of Plants Grown As Single Stem Cut Sprays In Barberton, Ohio Under Conditions As Described In Chart A.

We claim:

1. A new and distinct cultivar of *Chrysanthemum morifolium,* Ramat., plant known by the cultivar name Superstar and particularly characterized as to uniqueness by the combined characteristics of flat capitulum form; daisy capitulum type; white ray floret color; diameter across face of capitulum ranging from 100 to 120 mm. at maturity; uniform seven week photoperiodic flowering response to short days; tall plant height when grown as a single stem cut spray; and semi-upright branching pattern.

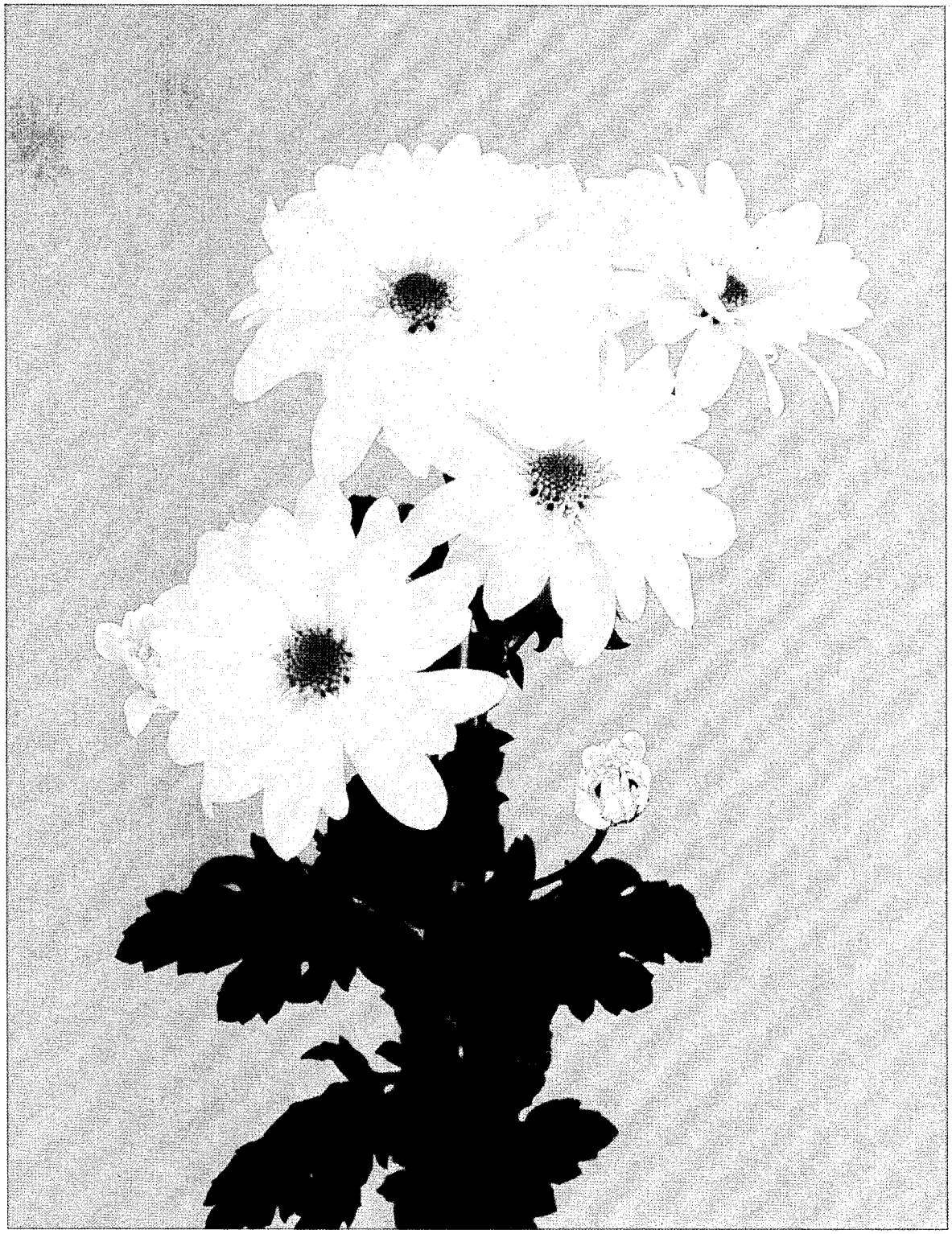

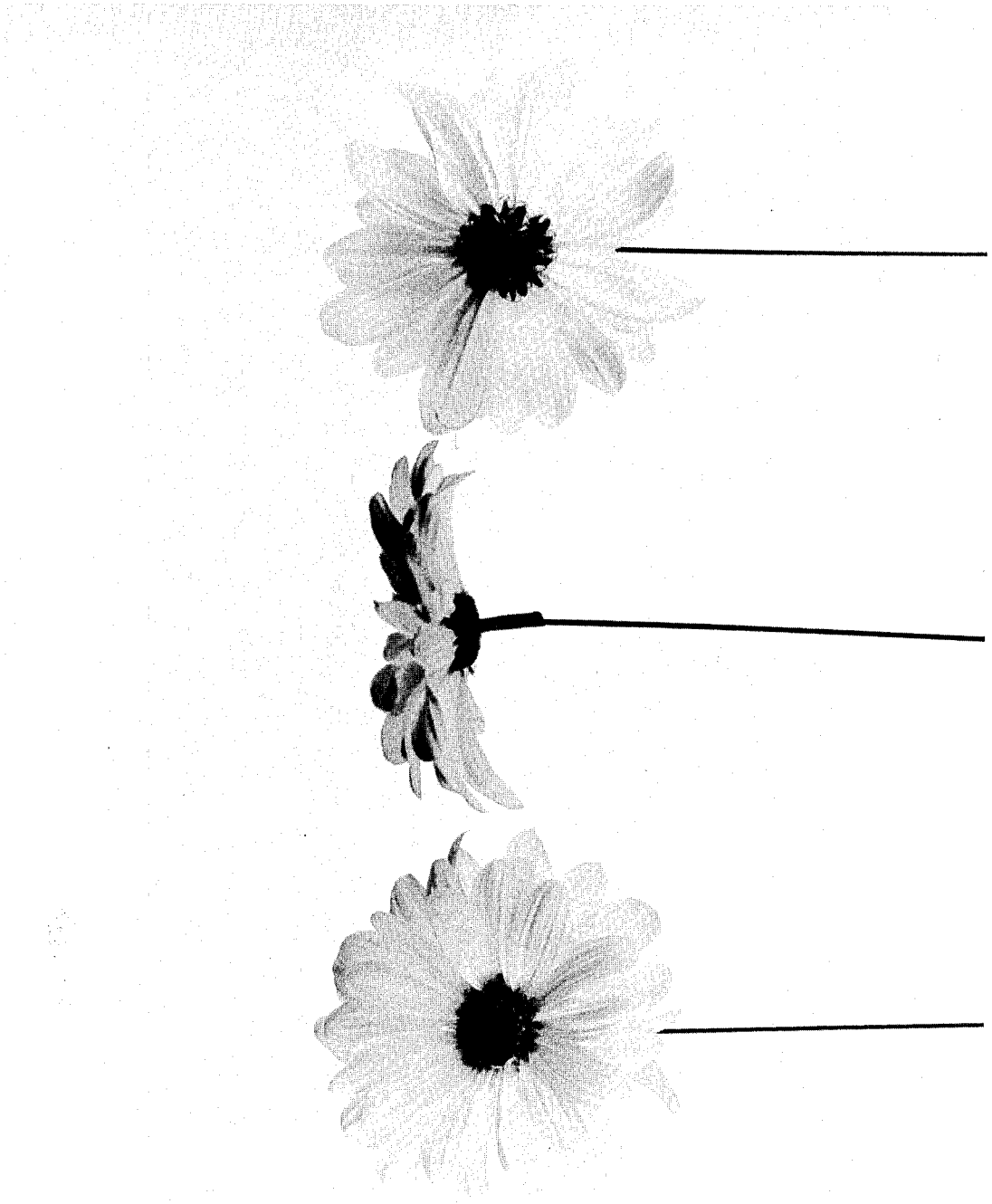

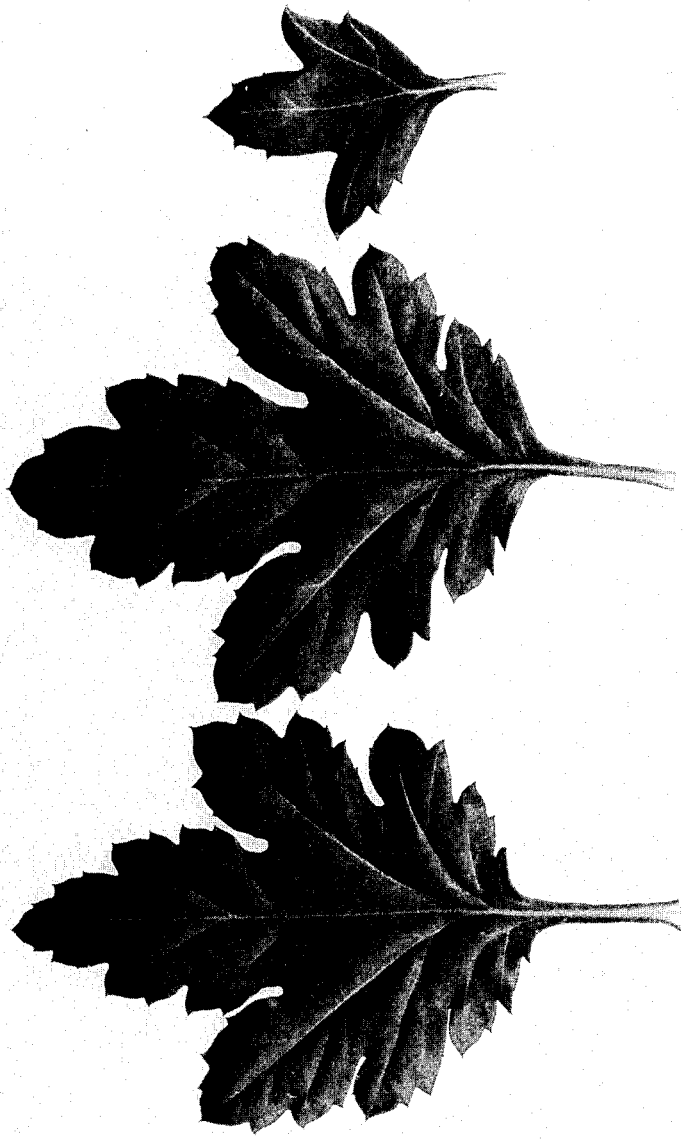

* * * * *